US011689799B2

(12) United States Patent
Wood et al.

(10) Patent No.: US 11,689,799 B2
(45) Date of Patent: Jun. 27, 2023

(54) COGNITIVE OPTICAL CONTROL SYSTEM AND METHODS

(71) Applicant: SYNAPTIVE MEDICAL INC., Toronto (CA)

(72) Inventors: Michael Frank Gunter Wood, Toronto (CA); Piotr Kuchnio, Toronto (CA); Cameron Anthony Piron, Toronto (CA)

(73) Assignee: Synaptive Medical Inc.

( * ) Notice: Subject to any disclaimer, the term of this patent is extended or adjusted under 35 U.S.C. 154(b) by 238 days.

(21) Appl. No.: 17/301,994

(22) Filed: Apr. 21, 2021

(65) Prior Publication Data

US 2021/0243358 A1    Aug. 5, 2021

Related U.S. Application Data

(63) Continuation of application No. 16/130,004, filed on Sep. 13, 2018, now Pat. No. 11,012,610.

(30) Foreign Application Priority Data

Sep. 27, 2017 (CA) .................. CA 2980396

(51) Int. Cl.
| | |
|---|---|
| *H04N 23/62* | (2023.01) |
| *A61B 34/00* | (2016.01) |
| *H04N 23/60* | (2023.01) |
| *H04N 23/72* | (2023.01) |
| *G06N 20/00* | (2019.01) |
| *G06N 5/04* | (2023.01) |
| *A61B 5/055* | (2006.01) |
| *A61B 5/00* | (2006.01) |

(Continued)

(52) U.S. Cl.
CPC ............. *H04N 23/62* (2023.01); *A61B 34/00* (2016.02); *A61B 34/25* (2016.02); *G01R 33/4812* (2013.01); *G01T 1/2985* (2013.01); *G06N 5/04* (2013.01); *G06N 20/00* (2019.01); *G16H 30/40* (2018.01); *H04N 23/64* (2023.01); *H04N 23/72* (2023.01); *A61B 5/055* (2013.01); *A61B 5/7264* (2013.01); *A61B 6/032* (2013.01); *A61B 6/481* (2013.01); *A61B 6/5247* (2013.01); *A61B 2505/05* (2013.01); *A61B 2576/026* (2013.01)

(58) Field of Classification Search
None
See application file for complete search history.

(56) References Cited

U.S. PATENT DOCUMENTS

2015/0173846 A1*  6/2015 Schneider ........ A61B 1/000095
                                                              600/424

OTHER PUBLICATIONS

Chen, C.H., Yao, T.K. and Kuo, C.M., Jun. 2013. Wide-angle camera distortion correction using neural back mapping. In 2013 IEEE International Symposium on Consumer Electronics (ISCE) (pp. 171-172). IEEE. (Year: 2013).*

* cited by examiner

*Primary Examiner* — Clifford Hilaire

(57) ABSTRACT

A cognitive optical system for dynamically refining imaging during a medical procedure, involving a processor operable by a set of executable instructions storable in relation to a non-transitory memory device. The processor is configured to automatically adjust an image by automatically compensating for at least one external factor affecting an anatomical area being viewed, automatically adjusting at least one imaging parameter, and automatically adjusting at least one internal control of an optical chain, whereby a quality of the image is improvable in real time.

20 Claims, 9 Drawing Sheets

(51) Int. Cl.
*A61B 6/00* (2006.01)
*A61B 6/03* (2006.01)
*G16H 30/40* (2018.01)
*G01R 33/48* (2006.01)
*G01T 1/29* (2006.01)

COGNITIVE OPTICAL CONTROL SYSTEM AND METHODS

CROSS-REFERENCE TO RELATED APPLICATION(S)

This document is a continuation application which claims the benefit of, and priority to: U.S. patent application Ser. No. 16/130,004, filed on Sep. 13, 2018, entitled "COGNITIVE OPTICAL CONTROL SYSTEM AND METHODS," and Canadian Patent Application No. 2,980,396, filed on Sep. 27, 2017, entitled "COGNITIVE OPTICAL CONTROL SYSTEM AND METHODS," all of which are incorporated herein by reference in their entirety.

FIELD

Generally, the present disclosure technically relates to medical imaging systems. More particularly, the present disclosure technically relates to control of optical systems for medical imaging systems. Even more particularly, the present disclosure technically relates to smart control of optical systems for medical imaging systems.

BACKGROUND

In the related art of surgery, imaging and imaging guidance is becoming a more significant component of clinical care, such as relating to disease diagnosis, disease monitoring, surgical approach planning, facilitating guidance during the procedure, and facilitating post-operative follow-up, or being a component of a multi-faceted treatment approach. Some related art systems involve integration of imaging data in a surgical suite for neurosurgery, wherein brain tumors are typically excised through an open craniotomy approach that is guided by a related art imaging device. The related art imaging device typically uses data from computerized tomography (CT) scans with an associated contrast (iodinated contrast) feature and magnetic resonance imaging (MRI) scans with associated contrast (gadolinium contrast). These related art systems involve registering the imaging data sets together, translating a three-dimensional imaging space to a three-dimensional space of a patient, tracking instruments relative to the patient, and the associating imaging data by way of an external hardware system, such as a mechanical arm, a radio-frequency device, or an optical tracking device. These related art systems have experienced many challenges. For instance, related art tissue visualization in operating rooms is frequently hindered by many factors outside control of an optical chain. Specifically, external factors, such as tissue composition and ambient lighting, negatively affect the ability of a user to differentiate various types of tissues within a visualized area of a surgical site. Therefore, a need exists for a smart optical control system and methods to overcome many of the related art challenges.

SUMMARY

In addressing at least many of the challenges experienced in the related art, the subject matter of the present disclosure involves a cognitive optical control system and methods for dynamically refining imaging during a medical procedure. In addressing some of the related art challenges, the cognitive optical control system and methods of the present disclosure generally involve optimization of imaging by using previously obtained and real-time information relating to ambient conditions and chemical composition of the tissue at a given surgical site. In addition, the cognitive optical control system and methods of the present disclosure use previous or "a priori" knowledge, such as previous or "a priori" information and previous or "a priori" data, relating to at least one factor, such as general anatomy, a patient's specific anatomy, geometry of an approach, lighting conditions, type of surgical tool, e.g., a pointer, a cutting tool, an aneurysm clip, etc., a position of a surgical tool, e.g., at or near a surface or a location at a given depth in a cavity, etc., and the like, to adaptively optimize at least one of an imaging system, an optical system, a lighting system, or a display system for a given medical or surgical procedure that a given user, such as a surgeon, is performing.

In accordance with an embodiment of the present disclosure, a cognitive optical system for dynamically refining imaging during a medical procedure, comprises: a processor operable by a set of executable instructions storable in relation to a non-transitory memory device and configured to automatically adjust an image by: automatically compensating for at least one external factor affecting an anatomical area being viewed; automatically adjusting at least one imaging parameter; and automatically adjusting at least one internal control of an optical chain, whereby quality of the image is improvable in real time.

In accordance with an embodiment of the present disclosure, a method of fabricating a cognitive optical system for dynamically refining imaging during a medical procedure, comprising: providing a processor operable by a set of executable instructions storable in relation to a non-transitory memory device and configured to automatically adjust an image by: automatically compensating for at least one external factor affecting an anatomical area being viewed; automatically adjusting at least one imaging parameter; and automatically adjusting at least one internal control of an optical chain, whereby quality of the image is improvable in real time.

In accordance with an embodiment of the present disclosure, a method of dynamically refining imaging during a medical procedure by way of a cognitive optical system, comprising: providing the cognitive optical system, providing the cognitive optical system comprising providing a processor operable by a set of executable instructions storable in relation to a non-transitory memory device and configured to automatically adjust an image by automatically compensating for at least one external factor affecting an anatomical area being viewed, automatically adjusting at least one imaging parameter, and automatically adjusting at least one internal control of an optical chain, whereby image quality is improvable in real time; automatically compensating for at least one external factor affecting an anatomical area being viewed; automatically adjusting at least one imaging parameter; and automatically adjusting at least one internal control of an optical chain, thereby improving quality of the image in real time.

Some of the features in the present disclosure are broadly outlined in order that the section entitled Detailed Description is better understood and that the present contribution to the art by the present disclosure is better appreciated. Additional features of the present disclosure are described hereinafter. In this respect, understood is that the subject matter of the present disclosure is not limited in its implementation to the details of the components or steps set forth herein or as illustrated in the several figures of the Drawing, but the subject matter is capable of being carried out in various ways which are also encompassed by the present disclosure. Also, understood is that the phraseology and terminology employed herein are for illustrative purposes in the description and are not regarded as limiting.

BRIEF DESCRIPTION OF THE DRAWING(S)

The above, and other, aspects, features, and advantages of several embodiments of the present disclosure will be more apparent from the following Detailed Description as presented in conjunction with the following several figures of the Drawing.

Figure 1:
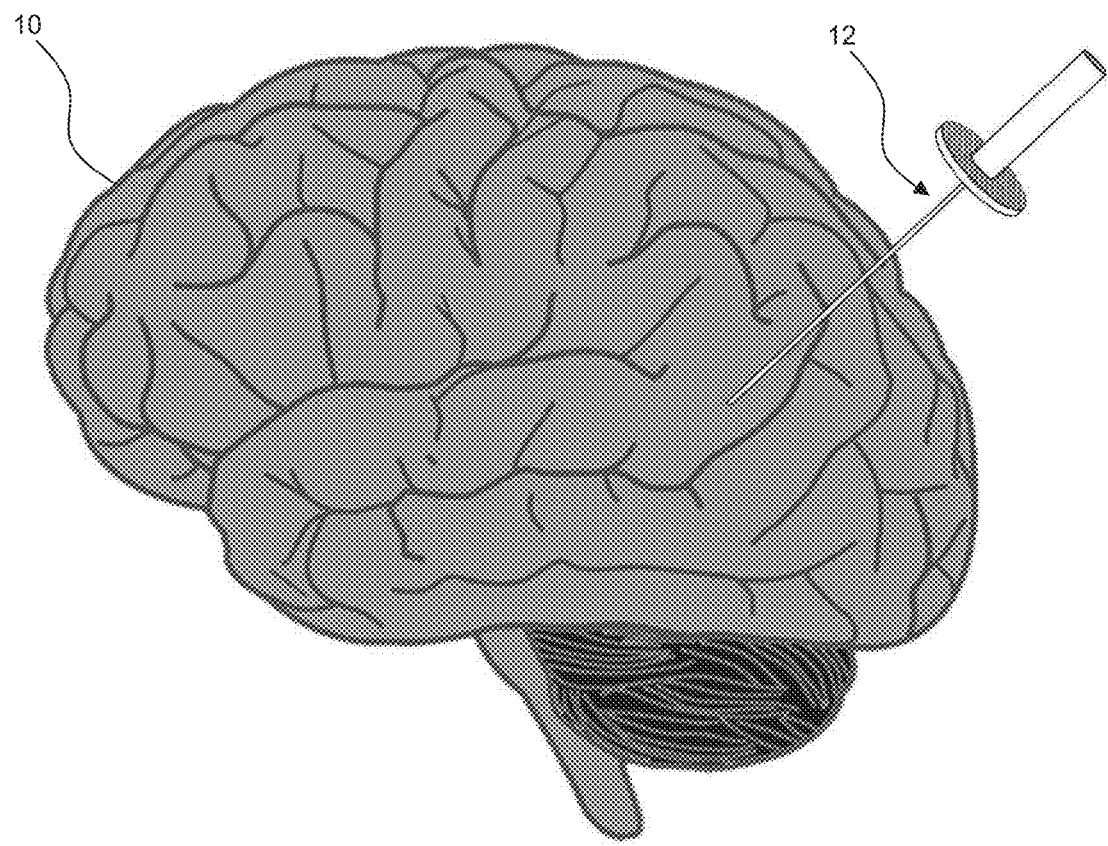
FIG. 1 is a diagram illustrating, in a side view, the insertion of an access port into a human brain, for providing access to internal brain tissue during a medical procedure, such as the NICO® BrainPath®, in accordance with an embodiment of the present disclosure.

Corresponding reference numerals or characters indicate corresponding components throughout the several figures of the Drawing. Elements in the several figures are illustrated for simplicity and clarity and have not necessarily been drawn to scale. For example, the dimensions of some elements in the figures are emphasized relative to other elements for facilitating understanding of the various presently disclosed embodiments. Also, common but well-understood elements that are useful or necessary in commercially feasible embodiment are often not depicted in order to facilitate a less obstructed view of these various embodiments of the present disclosure.

DETAILED DESCRIPTION

The systems and methods described herein are useful in the field of neurosurgery, including oncological care, neurodegenerative disease, stroke, brain trauma, and orthopedic surgery. The subject matter of the present disclosure is applicable to other conditions or fields of medicine. Noted is that, while the present disclosure describes examples in the context of neurosurgery, the subject matter of the present disclosure is applicable to other surgical procedures that may use intraoperative optical imaging.

Various example apparatuses or processes are below-described. No below-described example embodiment limits any claimed embodiment; and any claimed embodiments may cover processes or apparatuses that differ from those examples described below. The claimed embodiments are not limited to apparatuses or processes having all of the features of any one apparatus or process described below or to features common to multiple or all of the apparatuses or processes described below. The claimed embodiments optionally comprise any of the below-described apparatuses or processes.

Furthermore, numerous specific details are set forth in order to provide a thorough understanding of the disclosure. However, understood is that the embodiments described herein are practiced without these specific details. In other instances, well-known methods, procedures and components have not been described in detail so as not to obscure the embodiments described herein.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" or "example" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" is understood to mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Referring to FIG. 1, this diagram illustrates, in a side view, the insertion of an access port into a human brain, for providing access to internal brain tissue during a medical procedure, in accordance with an embodiment of the present invention. An access port 12 is inserted into a human brain 10, providing access to internal brain tissue. The access port 12 may include such instruments as catheters, surgical probes, or cylindrical ports, such as the NICO® BrainPath®. Surgical tools and instruments may then be inserted within the lumen of the access port in order to perform surgical, diagnostic, or therapeutic procedures, such as resecting tumors, as necessary. The present disclosure applies equally well to catheters, deep brain stimulation (DBS) needles, a biopsy procedure, and also to biopsies and/or catheters in other medical procedures performed on other parts of the body. In the example of a port-based surgery, a straight or linear access port 12 is typically guided down a sulcal path of the brain. Surgical instruments would then be inserted down the access port 12.

Figure 2:
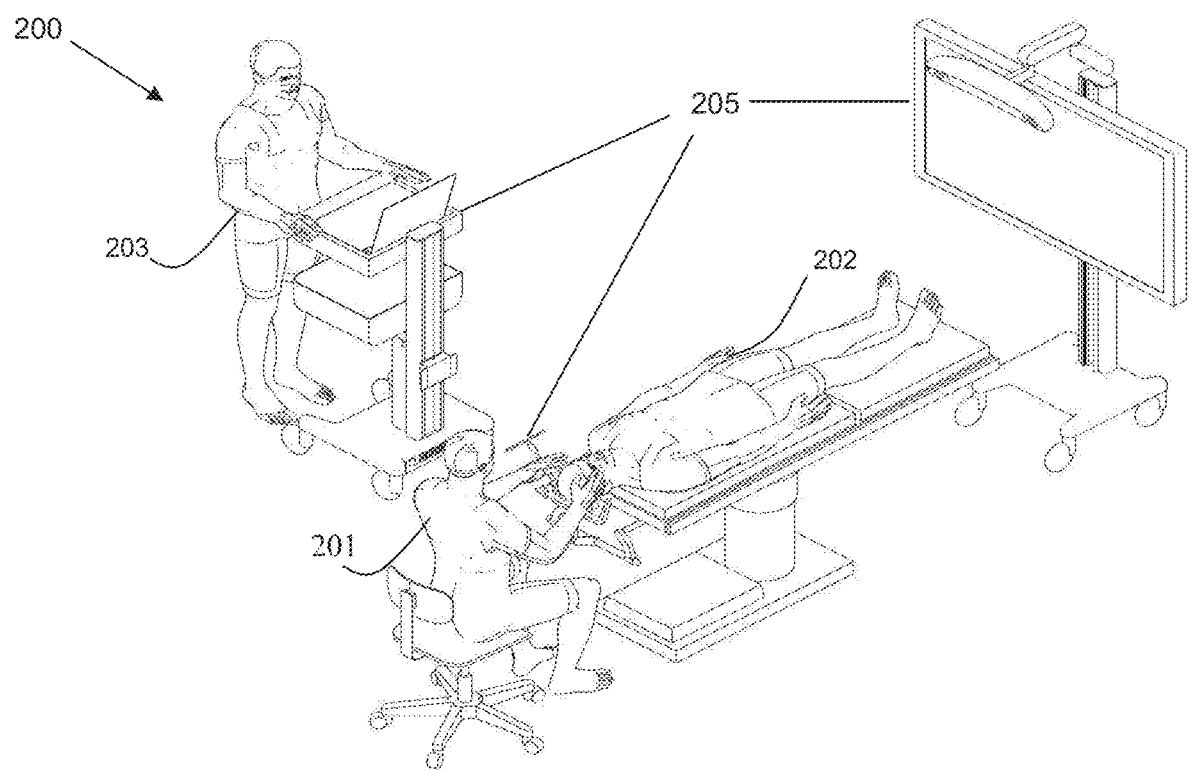
FIG. 2 is a diagram illustrating, in a perspective view, a surgical environment, such as an operating room, wherein an exemplary navigation system to support minimally invasive surgery may be implemented, in accordance with an embodiment of the present disclosure.

Referring to FIG. 2, this diagram illustrates, in a perspective view, a navigation system environment 200, wherein an exemplary medical navigation system 205 for supporting minimally invasive access port-based surgery is implemented, in accordance with an embodiment of the present disclosure. The exemplary navigation system environment 200 may be used to support navigated image-guided surgery. A surgeon 201 conducts a surgery on a patient 202 in an operating room (OR) environment. A medical navigation system 205 comprising an equipment tower (not shown), a tracking system 321 (FIG. 3), displays 311 and tracked instruments 360 assist the surgeon 201 during his procedure. An operator 203 is also present to operate, control, and assist the medical navigation system 205. The tracked instruments 360 may be calibrated by way of the calibration and methods as presently disclosed.

Figure 3:
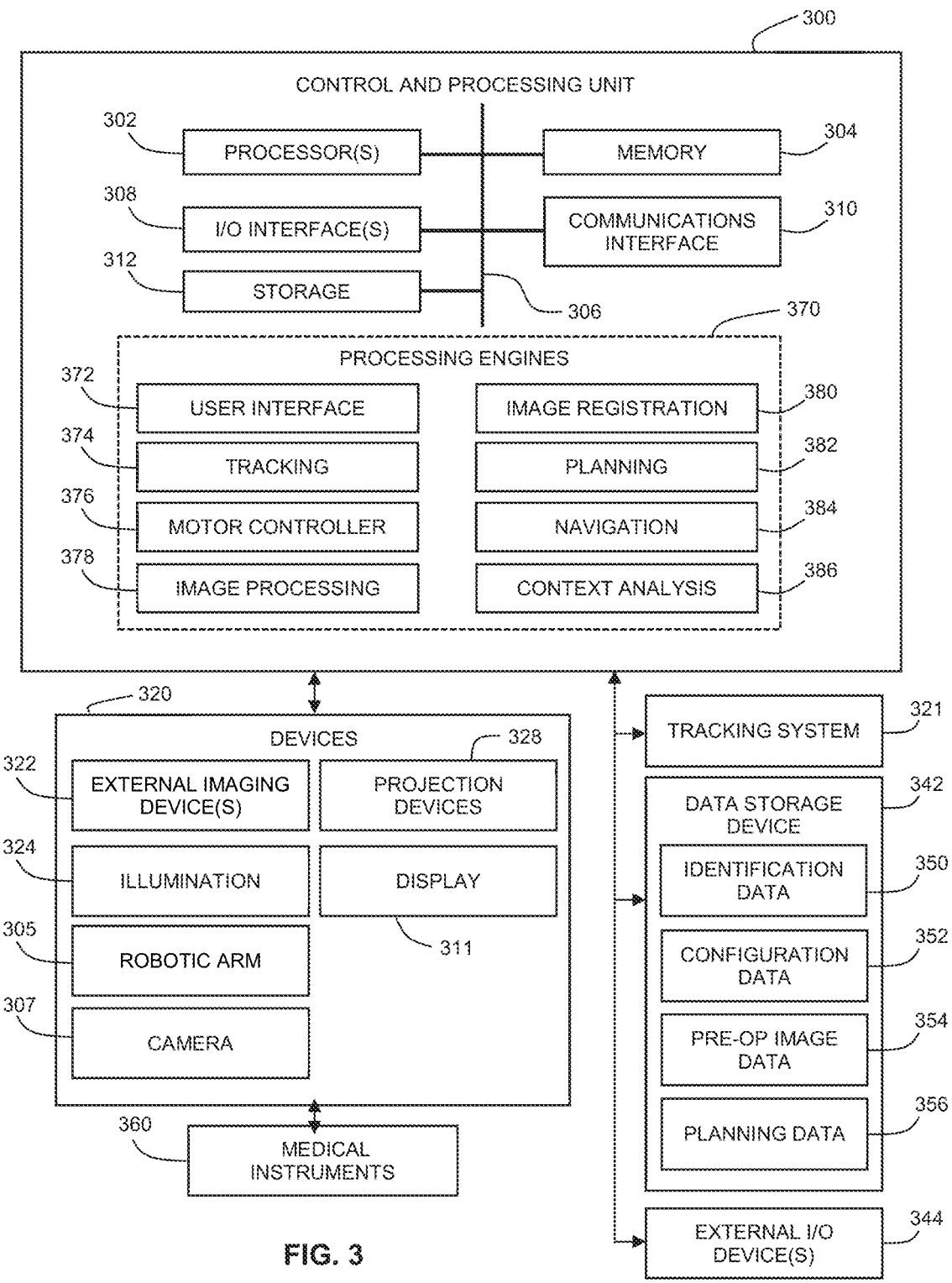
FIG. 3 is a block diagram illustrating a control and processing system useable in the navigation system, as shown in FIG. 2, in accordance with an embodiment of the present disclosure.

Referring to FIG. 3, this block diagram illustrates a control and processing system 300 operable in the medical navigation system 200, e.g., as part of the equipment tower, in accordance with an embodiment of the present disclosure. In one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device, e.g. a computer, hard drive, digital media device, or server, having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, understood is that in other embodiments, data storage device 342 may be provided as multiple storage devices.

Still referring to FIG. 3, the medical instruments 360 are identifiable by control and processing unit 300. The medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. For example, medical instruments 360 may include tracking spheres that may be recognizable by a tracking camera 307 and/or tracking system 321. In one example, the tracking camera 307 may be an infrared (IR) tracking camera. In another example, a sheath placed over a medical instrument 360 may be connected to and controlled by control and processing unit 300.

Still referring to FIG. 3, the control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, a robotic arm 305, one or more cameras 307, one or more projection devices 328, and one or more displays 311.

Still referring to FIG. 3, exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While the example processing modules are shown separately in FIG. 3, in one example the processing modules 370 may be stored in the memory 304 and the processing modules may be collectively referred to as processing modules 370.

Still referring to FIG. 3, understood is that the system is not intended to be limited to the components shown. One or more components of the control and processing system 300 may be provided as an external component or device. In one example, navigation module 384 may be provided as an external navigation system that is integrated with control and processing system 300.

Still referring to FIG. 3, some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

Still referring to FIG. 3, while some embodiments can be implemented in fully functioning computers and computer systems, various embodiments are capable of being distributed as a computing product in a variety of forms and are capable of being applied regardless of the particular type of machine or computer readable media used to actually effect the distribution.

Still referring to FIG. 3, at least some aspects disclosed can be embodied, at least in part, in software. That is, the techniques may be carried out in a computer system or other data processing system in response to its processor, such as a microprocessor, executing sequences of instructions contained in a memory, such as read only memory (ROM), volatile random access memory (RAM), non-volatile memory, cache or a remote storage device.

Still referring to FIG. 3, a computer readable storage medium can be used to store software and data which, when executed by a data processing system, causes the system to perform various methods. The executable software and data may be stored in various places including for example ROM, volatile RAM, non-volatile memory and/or cache. Portions of this software and/or data may be stored in any one of these storage devices.

Still referring to FIG. 3, examples of computer-readable storage media include, but are not limited to, recordable and non-recordable type media such as volatile and non-volatile memory devices, ROM, RAM, flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Still referring to FIG. 3, at least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

Still referring to FIG. 3, according to one aspect of the present application, one purpose of the navigation system 205 (FIG. 2), which may include control and processing unit 300, is to provide tools to the neurosurgeon that will lead to the most informed, least damaging neurosurgical operations. In addition to removal of brain tumours and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

Figure 4A:
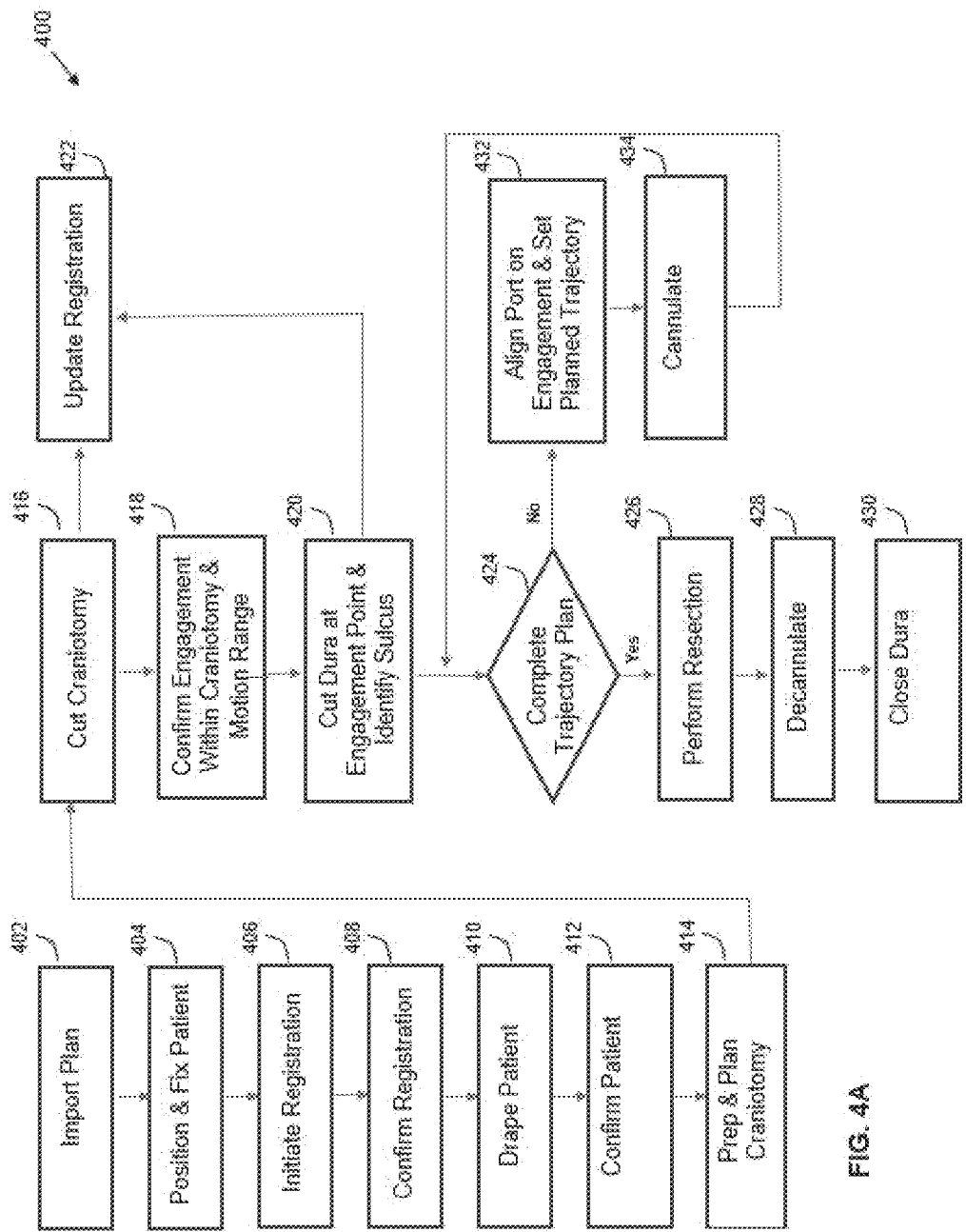
FIG. 4A is a flow diagram illustrating a method of using the navigation system, as shown in FIG. 2, for a surgical procedure, in accordance with an embodiment of the present disclosure.

Referring to FIG. 4A, this flow diagram illustrates a method 400 of performing a port-based surgical procedure by way of using a navigation system, such as the medical navigation system 205, as described in relation to FIG. 2, in accordance with an embodiment of the present disclosure. At a first block 402, the port-based surgical plan is imported. Once the plan has been imported into the navigation system at the block 402, the patient is affixed into position using a body holding mechanism 404. The head position is also confirmed with the patient plan in the navigation system, as indicated by block 404, which in one example may be implemented by the computer or controller forming part of the equipment tower (not shown). Next, registration of the patient is initiated, as indicated by block 406. The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Still referring to FIG. 4A, appreciated is that the present disclosure encompasses numerous registration techniques and at least one of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models used to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
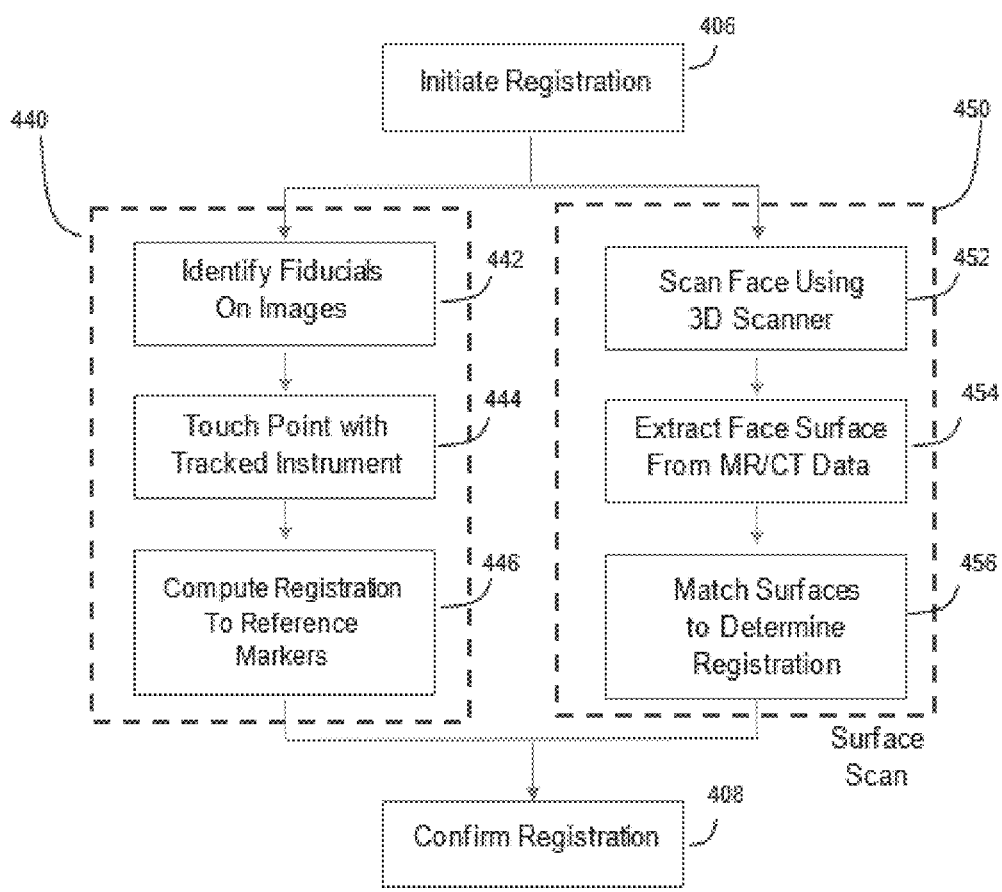
FIG. 4B is a flow diagram illustrating the step of registering a patient for a surgical procedure, in the method of using the navigation system, as shown in FIG. 4A, in accordance with an embodiment of the present disclosure.

Referring to FIG. 4B, this flow chart illustrates the step of registering a patient for a surgical procedure, as indicated by block 406, in the method 400 of using the navigation system, as shown in FIG. 4A, in greater detail, in accordance with an embodiment of the present disclosure. If the use of fiducial touch points 440 is contemplated, the method involves first identifying fiducial markers on images, as indicated by block 442, then touching the touch points with a tracked instrument, as indicated by block 444. Next, the navigation system computes the registration to reference markers, as indicated by block 446. Of course, the medical navigation system 205 has to know the relationship of the tip of tracked instrument relative to the tracking markers of the tracked instrument with a high degree of accuracy for the blocks 444 and 446 to provide useful and reliable information to the medical navigation system 205. An example tracked instrument is discussed below with reference to FIG. 5 and a calibration apparatus for verifying and establishing this relationship is discussed below in connection with FIGS. 6-8.

Still referring to FIG. 4B, alternately, registration can also be completed by conducting a surface scan procedure, as indicated by block 450. The block 450 is presented to show an alternative approach, but may not typically be used when using a fiducial pointer. First, the face is scanned using a 3D scanner, as indicated by block 452. Next, the face surface is extracted from MR/CT data, as indicated by block 454. Finally, surfaces are matched to determine registration data points, as indicated by block 456. Upon completion of either the fiducial touch points 440 or surface scan 450 procedures, the data extracted is computed and used to confirm registration at block 408, shown in FIG. 4A.

Still referring to FIG. 4B and referring back to FIG. 4A, once registration is confirmed, as indicated by block 408, the patient is draped, as indicated by block 410. Typically, draping involves covering the patient and surrounding areas with a sterile barrier to create and maintain a sterile field during the surgical procedure. The purpose of draping is to eliminate the passage of microorganisms, e.g., bacteria, between non-sterile and sterile areas. At this point, conventional navigation systems require that the non-sterile patient reference is replaced with a sterile patient reference of identical geometry location and orientation. Numerous mechanical methods may be used to minimize the displacement of the new sterile patient reference relative to the non-sterile one that was used for registration but it is inevitable that some error will exist. This error directly translates into registration error between the surgical field and pre-surgical images. In fact, the further away points of interest are from the patient reference, the worse the error will be.

Still referring to FIG. 4B and referring back to FIG. 4A, upon completion of draping, as indicated by block 410, the patient engagement points are confirmed, as indicated by block 412, and then the craniotomy is prepared and planned, as indicated by block 414. Upon completion of the preparation and planning of the craniotomy, as indicated by block 414, the craniotomy is cut and a bone flap is temporarily removed from the skull to access the brain, as indicated by block 416. Registration data is updated with the navigation system at this point, as indicated by block 422. Next, the engagement within craniotomy and the motion range are confirmed, as indicated by block 418. Next, the procedure advances to cutting the dura at the engagement points and identifying the sulcus, as indicated by block 420.

Still referring to FIG. 4B and referring back to FIG. 4A, thereafter, the cannulation process is initiated via the trajectory plan, as indicated by block 424. Cannulation involves inserting a port into the brain, typically along a sulci path as identified at 420, along a trajectory plan. Cannulation is typically an iterative process that involves repeating the steps of aligning the port on engagement and setting the planned trajectory, as indicated by block 432, and then cannulating to the target depth, as indicated by block 434, until the complete trajectory plan is executed, as indicated by block 424.

Still referring to FIG. 4B and referring back to FIG. 4A, once cannulation is complete, the surgeon then performs resection, as indicated by block 426, to remove part of the brain and/or tumor of interest. The surgeon then decannulates, as indicated by block 428, by removing the port and any tracking instruments from the brain. Finally, the surgeon closes the dura and completes the craniotomy, as indicated by block 430. Some aspects, shown in FIG. 4A, are specific to port-based surgery, such as portions indicated by blocks 428, 420, and 434, but the appropriate portions of these steps may be skipped or suitably modified when performing non-port based surgery.

Still referring to FIG. 4B and referring back to FIG. 4A, when performing a surgical procedure using a medical navigation system 205, the medical navigation system 205 must acquire and maintain a reference of the location of the tools in use as well as the patient in three dimensional (3D) space. In other words, during a navigated neurosurgery, there needs to be a tracked reference frame that is fixed relative to the patient's skull. During the registration phase of a navigated neurosurgery, as indicated by block 406, a transformation is calculated that maps the frame of reference of preoperative MRI or CT imagery to the physical space of the surgery, specifically the patient's head. This may be accomplished by the navigation system 205 tracking locations of markers fixed to the patient's head, relative to the static patient reference frame. The patient reference frame is typically rigidly attached to the head fixation device, such as a Mayfield clamp. Registration is typically performed before the sterile field has been established, as indicated by block 410.

Figure 5:
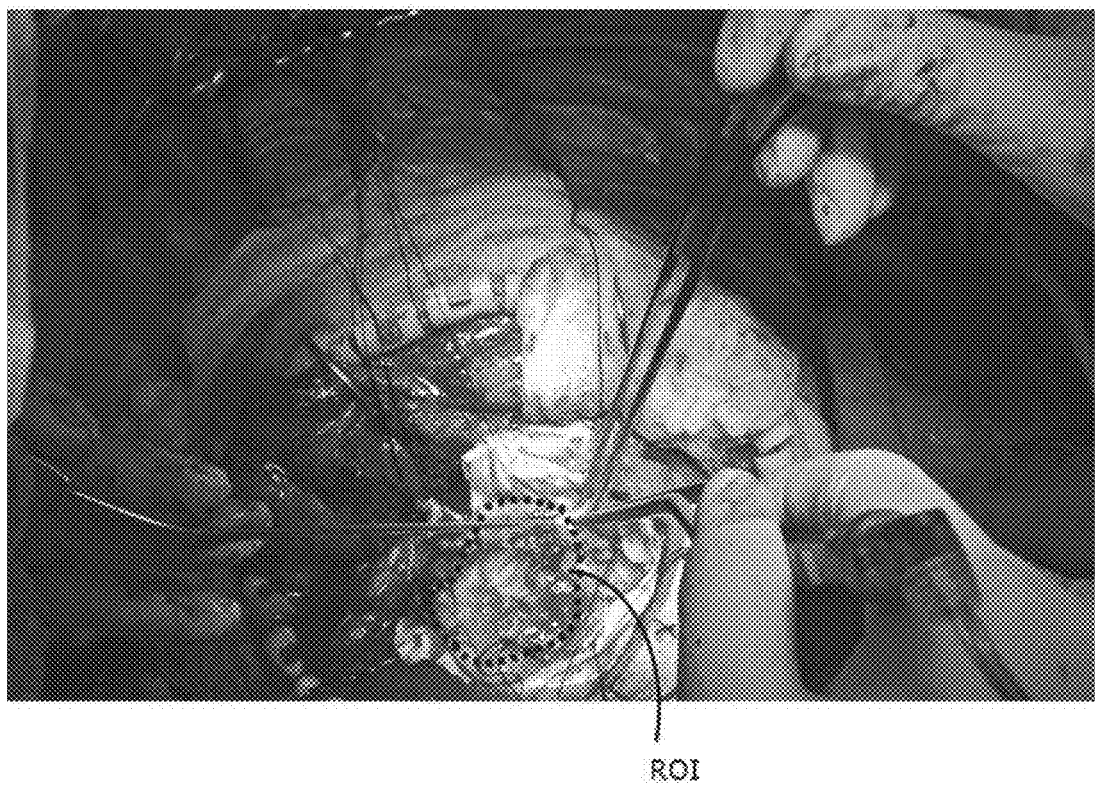
FIG. 5 is a diagram illustrating a perspective view of an implementation of a cognitive optical system for dynamically refining imaging during a medical procedure, in accordance with an embodiment of the present disclosure.

Referring to FIG. 5, this diagram illustrates, in a perspective view, an implementation of a cognitive optical system S (FIGS. 6-8) for dynamically refining imaging during a medical procedure, in this example, neurosurgery. As shown, the area indicated by the dotted lines is designated as a region-of-interest ROI, wherein the processor 10 (FIG. 6) of the system S (FIG. 6) is configured to fine tune an optical change in relation to parameters, such as color, saturation, brightness, contrast, and the like. The processor 10 is configured to recognize an ROI by way of a medical tool, such as a pointer tool, wherein an enhanced image is displayed corresponding to the area indicated by the pointer tool.

Figure 6:
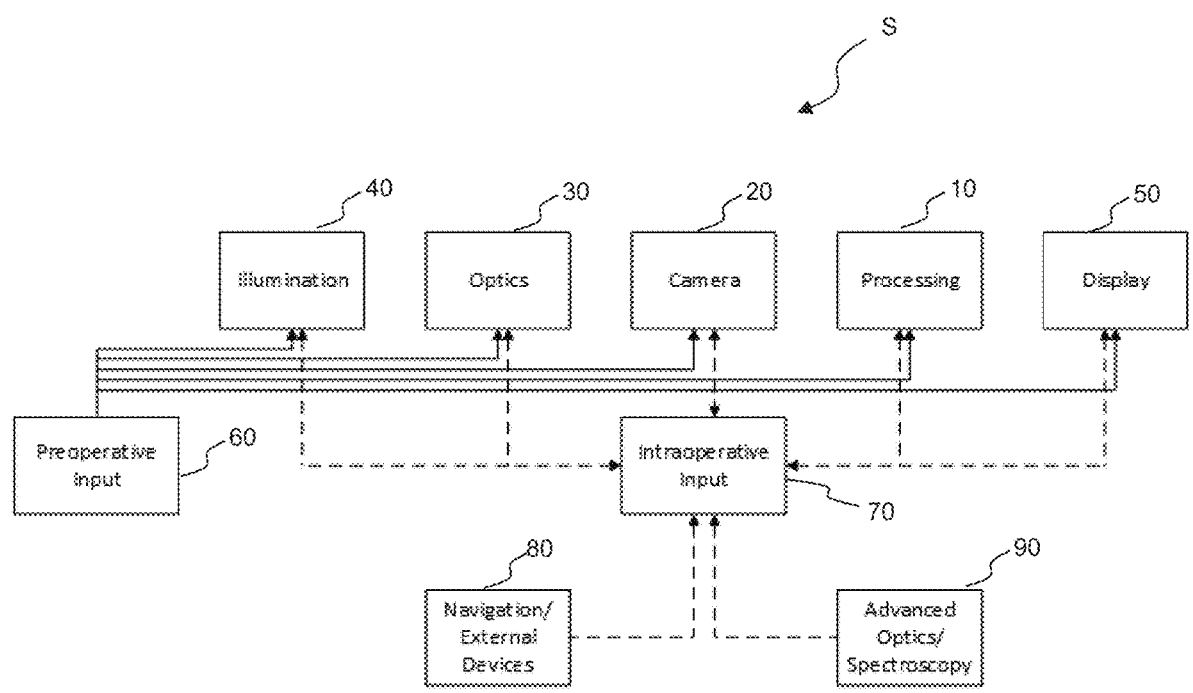
FIG. 6 is a schematic diagram illustrating a cognitive optical system for dynamically refining imaging during a medical procedure, in accordance with an embodiment of the present disclosure.

Referring to FIG. 6, this schematic diagram illustrates a cognitive optical system S for dynamically refining imaging during a medical procedure, in accordance with an embodiment of the present disclosure. The system S generally comprises: a processor 10 operable by a set of executable instructions storable in relation to a non-transitory memory device (not shown) and configured to automatically adjust an image by: automatically compensating for at least one external factor affecting an anatomical area being viewed; automatically adjusting at least one imaging parameter; and automatically adjusting at least one internal control of an optical chain, whereby a quality of the image is improvable in real time.

Still referring to FIG. 6, the system S further comprises at least one of a camera device or system 20, an optics device or system 30, an illumination device or system 40, a display device or system 50, a preoperative input device 60, an intraoperative input device 70, at least one external navigation device or system 80 and at least one advanced optical or spectroscopic device or system 90, in accordance with embodiments of the present disclosure. The intraoperative input device 70 is configured to receive input from at least one external navigation device or system 80 and at least one advanced optical or spectroscopic device or system 90. Each of the processor 10, the camera device 20, the optics device 30, an illumination device 40, and a display device 50 is configured to receive input from the preoperative input device 60 as well as to receive input from, and transmit output to, the intraoperative input device 70.

Still referring to FIG. 6, in the system S, the optical chain comprises at least one of component of optics, mechanical hardware, electronic hardware, firmware, and software. The at least one imaging parameter comprises at least one of illumination, saturation, color, contrast, and opacity. The processor 10 is configured to at least one of: automatically adjust illumination by adjusting at least one of an illumination spectrum and a luminance in relation to the camera device 20, such as a camera scope, automatically adjust color by adjusting color filters in relation to the camera device 20, such as the camera scope, automatically adjust saturation by processing the image to reduce light, and automatically adjust opacity by at least one of adjusting an infrared illumination level and applying a filter. The processor 10 is configured to automatically adjust an image based on at least one input parameter comprising at least one of a host tissue type, a pathology type, an environmental condition, an optical chain variable, and a plurality of user experience data, such as via the preoperative input device 60.

Still referring to FIG. 6, in the system S, the processor 10 utilizes a machine learning technique, and/or any other artificial intelligence technique, to automatically adjust the image based on the at least one input parameter by fine tuning the optical chain. The processor 10 is configured to learn from data relating to sources, such as informatics, pathological information, past surgical information, and the like, for facilitating and/or accelerating the medical procedure, such as neurosurgery. By using the machine learning technique, the processor 10 is configured to learn without being explicitly programmed and its functions are not limited by the set of executable instructions. The processor 10 is configured to learn from, and make predictions based on, data, such as past data and real-time data, thereby making data-driven predictions, or determinations, e.g., via building a model from sample inputs, and thereby overcoming strict adherence to the set of executable instructions. Machine learning is employed by the processor 10 in a range of operations, wherein an explicit set of executable instructions for a given operation is infeasible, e.g., in relation to computer vision or imaging.

Still referring to FIG. 6, in the system S, the processor 10 utilizes a machine learning technique, involving computational statistics, which also focuses in prediction-making, e.g., involving mathematical optimization. The machine learning technique may also comprise data mining techniques, involving an exploratory data analysis or an unsupervised learning technique. The machine learning technique may also involve learning and establishing baseline behavioral profiles for various entities or subjects, e.g., patients, and then use the baseline behavioral profiles to find meaningful anomalies. The exploratory data analytics facilitates developing complex models and updatable instructions for prediction, e.g., via predictive analytics. These analytical models allow the processor 10 to provide medical professionals, such as surgeons, with reliable and repeatable decisions and to develop insights through learning from historical relationships and data trends. The machine learning technique comprises at least one technique of: decision tree learning, association rule learning, deep learning, inductive logic programming, support vector machines, clustering, Bayesian networks, reinforcement learning, representation learning, similarity and metric learning, sparse dictionary learning, Genetic algorithms, rule-based machine learning, and learning classifier.

Still referring to FIG. 6, in the system S, the set of executable instructions comprises a predictive macro-optimization instruction based on a multi-modal real-time tissue interrogation for facilitating dynamically refining imaging. The predictive macro-optimization instruction comprises informatics, whereby the processor 10 is configured to determine at least one ideal condition corresponding to the at least one external factor. The processor 10 is configured to instruct an imaging device or system, such as the camera device 20, to provide a prompt requesting approval of an automated adjustment of the at least one imaging parameter prior to rendering an adjusted image on the display device 50.

Still referring to FIG. 6, in the system S, the informatics comprises a feature for learning information relating to previous procedures. The information relating to previous procedures comprises at least one type of imaging parameter for optimizing tissue differentiation. The at least one internal control of the optical chain comprises at least one of a zoom level, a numerical aperture, a camera type, an exposure time, an exposure gain, a de-noising strength, a local area contrast enhancement strength, a display type, a brightness level, and contrast level.

Still referring to FIG. 6, the cognitive optical system S generally improves image quality by automatically adjusting internal controls of the optical chain (hardware, firmware, and software) to compensate for external factors that affect an area of a surgical site being viewed, whereby a surgeon's ability to view anatomy is improvable, in accordance with some embodiments of the present disclosure. For example, ambient conditions in the environment surrounding tissue at a surgical site may cause increased illumination, thereby saturating the tissue being imaged, e.g., when a headlamp is being used. Such additional illumination is adjustable by way of the cognitive optical system S by adjusting the illumination spectrum and luminance output by the camera device 20, e.g., the camera scope, by adjusting colour filters in the camera scope, and/or by processing the image to reduce the presence of such light. In another example, the cognitive optical system S is implementable if blood is saturating a field of view (FoV) at a surgical site, e.g., automatically detecting whether excess blood is present and adjusting, e.g., automatically adjusting infrared illumination level to reduce opaqueness of the excess blood. Alternatively, the cognitive optical system S uses a filter to reduce the opaqueness.

Still referring to FIG. 6, such adjustments to the optical chain are dynamically performed by the cognitive optical system S; and, in some embodiments, such adjustments to the optical chain are performed in real-time, whereby visualization of the tissue of interest is constantly being re-enhanced. Also, noteworthy is that at least the following factors are considered by the cognitive optical system S as adjustable inputs: type of host tissue, type of pathology, ambient and local environmental conditions, optical chain variables, information relating to a plurality of user experiences (or transactions), wherein a predictive macro optimization comprising a dynamic refinement is provided based on multi-modal real-time tissue interrogation.

Still referring to FIG. 6, the cognitive optical system S, comprising the processor 10, is implementable in the context of informatics, wherein the processor 10 learns the ideal conditions relating to a set of specific external factors. For example, glioblastomas or "gliomas" (GBMs) have been imaged, e.g., by way of an imaging system, wherein the ideal lighting conditions to best view these gliomas have been determined. The cognitive optical system S is implementable with the imaging system to verify whether tissue at a given surgical site has a GBM at any time an external measurement is taken of an imaged area. In another example, if a Raman signal indicates that a given portion of tissue indicates at least one of a tumor or a necrotic tissue section, the cognitive optical system S is configured to automatically alter the spectrum of light to maximize differentiability between healthy and unhealthy tissue (such as the tumor or necrotic tissue section) by rendering a boundary more visible therebetween than hitherto possible by using related art optical systems.

Still referring to FIG. 6, the cognitive optical system S involves an adjustment of parameters, such as incident lighting, via the illumination device 40. However, in implementing some embodiments of the present disclosure, wherein factors, such as tissue composition, are not adjustable, the processor 10 is configured to adjust a plurality of optical parameters, e.g., for use by the optics device 30, to render at least one optimized image on the display device 50, wherein the at least one optimized image comprises at least one of a "true" image of the tissue (as seen by a true source, such as at least one of a naked eye and a spectroscopic image of viewed tissue), and an enhanced image for facilitating optimized tissue differentiation, whereby surgical performance is improvable.

Still referring to FIG. 6, noteworthy is that any automated adjustment of imaging parameters should be approved by a surgeon, such as by way of a prompt from the optical system S prior to rendering the at least one optimized image on the display device 50. The optical system S is configured to learn information from previous procedures, such as the types of imaging parameters that are likely to provide an image which facilitates the best or optimized tissue differentiation. For example, if the tissue of interest is preoperatively known by the system S as a glioma, the processor 10 is configured to adjust at least one imaging parameter to acquire an image, whereby imaging of the glioma is optimized. In another example, the processor 10 is configured to consider outcomes of previous procedures and to determine what imaging parameters influence better or optimized imaging outcomes. In yet another example, the processor 10 of the system S is configured to consider and/or analyze a plurality of "glioma" images taken, e.g., by way of an imaging system, whereby analyzed information is provided, and to cross-correlate such analyzed information with a set of optical parameters resulting in the best or optimized imaging, e.g., by way of an imaging system. The processor 10 of the system S uses the set of optical parameters, resulting in the best or optimized imaging, to adjust at least one imaging parameter of the optical chain in relation to a given pathology, e.g., a glioma.

Still referring to FIG. 6, when searching for brain tumors, the processor 10 of the system S is configured to enhance colour contrast in at least one of the highlights and the mid-tones of an acquired image. In other embodiments, the processor 10 of the system S is configured to adjust other available parameters in relation to a given type of surgery. In some embodiments, the processor 10 of the system S is configured to use a hierarchal structure for performing any dynamic parameter adjustment. The use of a hierarchical structure is important in the system S for at least that, in some surgical cases, optimizing one part of the optical chain, after a different optimization has already been achieved, may otherwise cause a situation wherein optimization of one parameter results in a degradation of another parameter.

Figure 7:
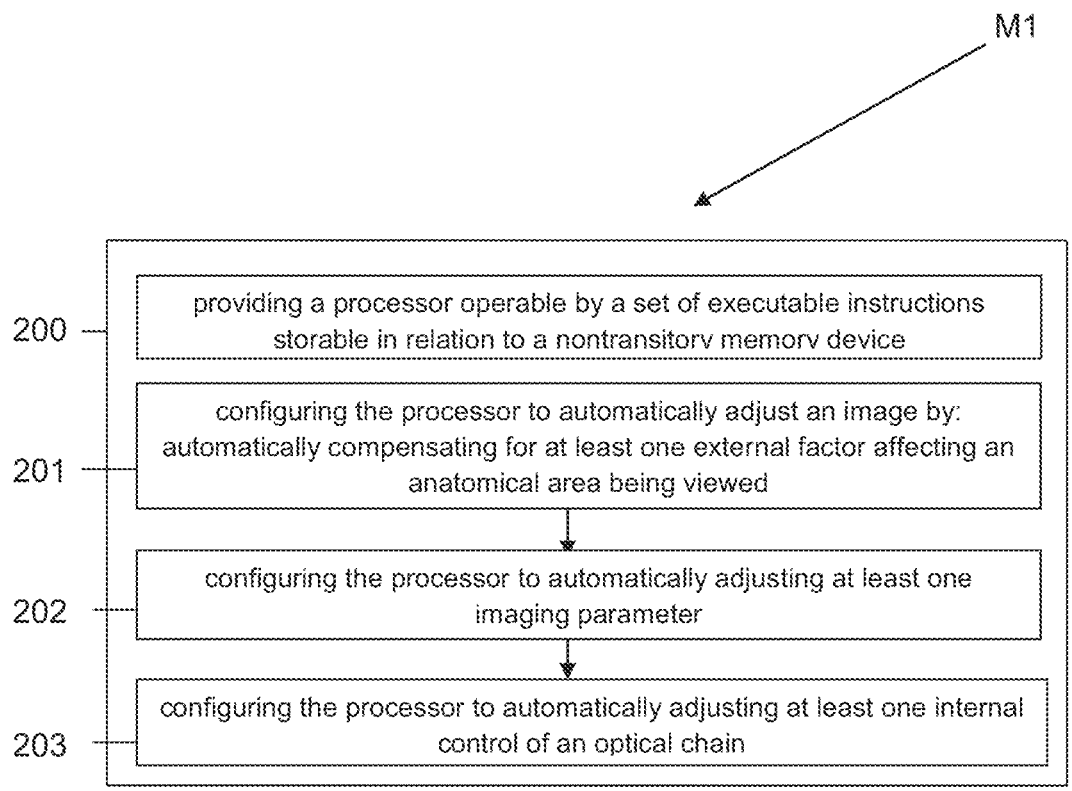
FIG. 7 is a flow diagram illustrating a method of fabricating a cognitive optical system for dynamically refining imaging during a medical procedure, in accordance with an embodiment of the present disclosure.

Referring to FIG. 7, and referring back to FIG. 6, this flow diagram illustrates a method M1 of fabricating a cognitive optical system S for dynamically refining imaging during a medical procedure, in accordance with an embodiment of the present disclosure. The method M1 generally comprises: providing a processor 10 operable by a set of executable instructions storable in relation to a non-transitory memory device, as indicated by block 200, and configured to automatically adjust an image by: automatically compensating for at least one external factor affecting an anatomical area being viewed, as indicated by block 201; automatically adjusting at least one imaging parameter, as indicated by block 202; and automatically adjusting at least one internal control of an optical chain, as indicated by block 203, whereby a quality of the image is improvable in real time.

Still referring to FIG. 7, and referring back to FIG. 6, in the method M1, providing the processor 10 comprises configuring the processor 10 to automatically adjust the at least one internal control of the optical chain comprising at least one of optical hardware (not shown), optical firmware (not shown), or optical software component (not shown). Providing the processor 10 comprises configuring the processor 10 to automatically adjust the at least one imaging parameter comprising at least one of illumination, saturation, color, contrast, or opacity, and wherein providing the processor 10 comprises configuring the processor 10 to at least one of: automatically adjust illumination by adjusting at least one of an illumination spectrum or a luminance in relation to a camera device 20, e.g., a camera scope; automatically adjust color by adjusting color filters in relation to the camera device 20, e.g., the camera scope; automatically adjust saturation by processing the image to reduce light; and automatically adjust opacity by at least one of adjusting an infrared illumination level or applying a filter.

Still referring to FIG. 7, and referring back to FIG. 6, in the method M1, providing the processor 10 comprises configuring the processor 10 to automatically adjust an image based on at least one input parameter comprising at least one of a host tissue type, a pathology type, an environmental condition, an optical chain variable, or a plurality of user experience data. Providing the processor 10 comprises configuring the processor 10 as operable by the set of executable instructions comprising a predictive macro-optimization instruction based on a multi-modal real-time tissue interrogation for facilitating dynamically refining imaging. Providing the processor 10 comprises configuring the processor 10 as operable by the set of executable instructions comprising a predictive macro-optimization instruction comprising informatics, whereby the processor 10 is configured to determine at least one ideal condition corresponding to the at least one external factor.

Still referring to FIG. 7 and referring back to FIG. 6, in the method M1, providing the processor 10 comprises configuring the processor 10 to instruct an imaging system to provide a prompt requesting approval of an automated adjustment of the at least one imaging parameter prior to rendering an adjusted image on a display device 50. Providing the processor 10 comprises configuring the processor 10 as operable by the set of executable instructions comprising a predictive macro-optimization instruction, the predictive macro-optimization instruction comprising informatics, the informatics comprising a feature for learning information relating to previous procedures, and the information relating to previous procedures comprises at least one type of imaging parameter for optimizing tissue differentiation. The at least one internal control of the optical chain comprises at least one of a zoom level, a numerical aperture, a camera type, an exposure time, an exposure gain, a de-noising strength, a local area contrast enhancement strength, a display type, a brightness level, or contrast level.

Figure 8:
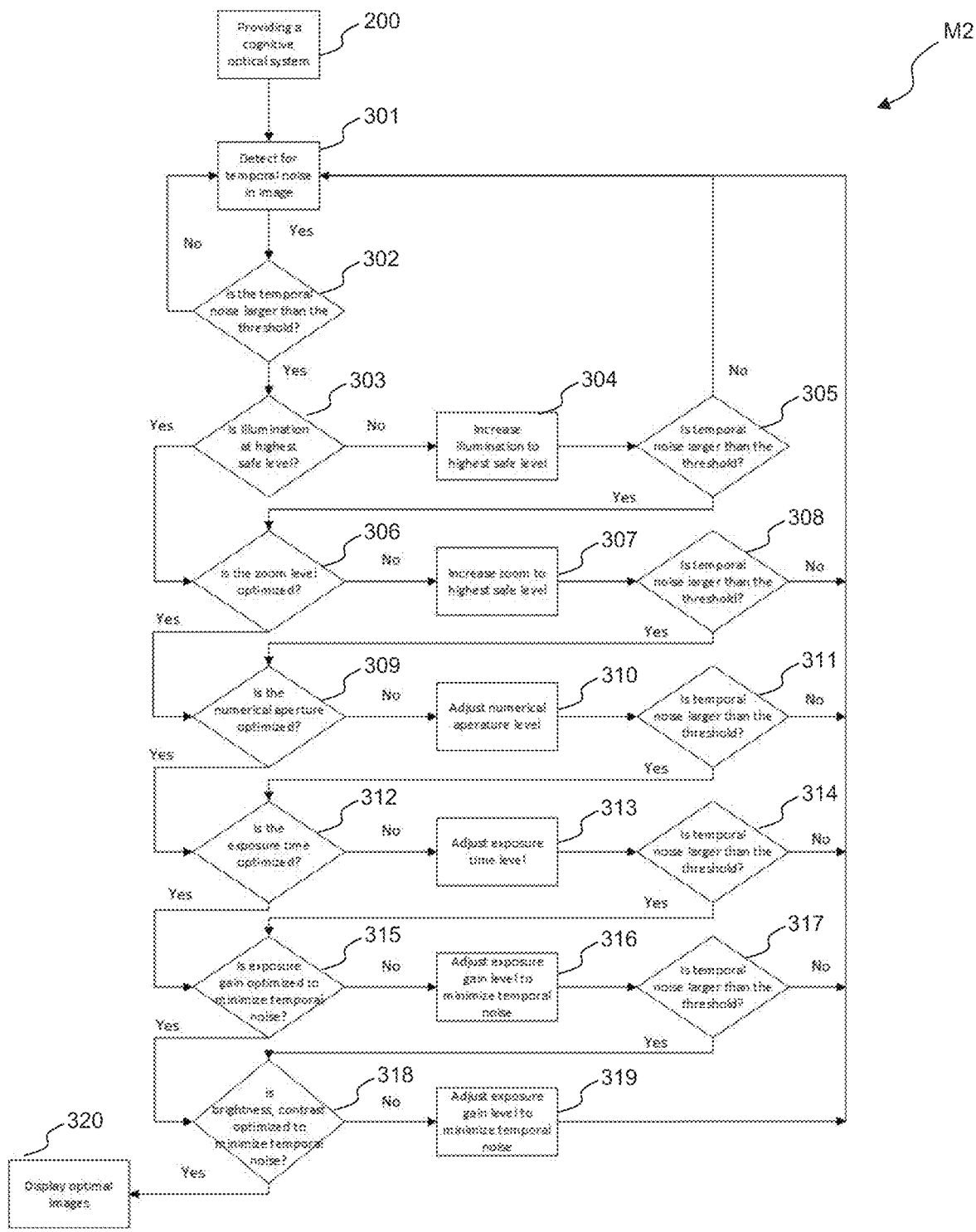
FIG. 8 is a flow diagram illustrating a method of dynamically refining imaging during a medical procedure by way of a cognitive optical system, in accordance with an embodiment of the present disclosure.

Referring to FIG. 8, and referring back to FIG. 7, this flow diagram illustrates a method M2 of dynamically refining imaging during a medical procedure by way of a cognitive optical system, in accordance with an embodiment of the present disclosure. The method M2 generally comprises: providing the cognitive optical system S, as indicated by block 200, providing the cognitive optical system S comprising providing a processor 10 operable by a set of executable instructions storable in relation to a non-transitory memory device (not shown) and configured to automatically adjust an image by automatically compensating for at least one external factor affecting an anatomical area being viewed, as indicated by block 201, automatically adjusting at least one imaging parameter, as indicated by block 202, and automatically adjusting at least one internal control of an optical chain, as indicated by block 203, whereby image quality is improvable in real time; automatically compensating for at least one external factor affecting an anatomical area being viewed; automatically adjusting at least one imaging parameter; and automatically adjusting at least one internal control of an optical chain, thereby improving quality of the image quality in real time.

Still referring to FIG. 8, the method M2 further comprises: detecting temporal noise in an image, as indicated by block 301; determining whether the temporal noise exceeds a given threshold, as indicated by block 302; if the temporal noise fails to exceed the given threshold, detecting temporal noise in an image, as indicated by block 301, or, if the temporal noise exceeds the given threshold, determining whether illumination is occurring at a maximum safe illumination level, as indicated by block 303; increasing illumination to a maximum safe illumination level, as indicated by block 304; determining whether the temporal noise exceeds the given threshold, as indicated by block 305; if the temporal noise fails to exceed the given threshold, detecting temporal noise in the image, as indicated by block 301, or, if the temporal noise exceeds the given threshold, determining whether a zoom level is optimized, as indicated by block 306; adjusting the zoom level to a maximum safe zoom level, as indicated by block 307; determining whether the temporal noise exceeds a given threshold, as indicated by block 308; if the temporal noise fails to exceed the given threshold, detecting temporal noise in an image, as indicated by block 301, or, if the temporal noise exceeds the given threshold, determining whether a numerical aperture is optimized, as indicated by block 309; adjusting the numerical aperture, as indicated by block 310; determining whether the temporal noise exceeds a given threshold, as indicated by block 311; if the temporal noise fails to exceed the given threshold, detecting temporal noise in an image, as indicated by block 301, or, if the temporal noise exceeds the given threshold, determining whether an exposure time is optimized, as indicated by block 312; adjusting the exposure time level, as indicated by block 313; determining whether the temporal noise exceeds a given threshold, as indicated by block 314; if the temporal noise fails to exceed the given threshold, detecting temporal noise in an image, as indicated by block 301, or, if the temporal noise exceeds the given threshold, determining whether an exposure gain is optimized, as indicated by block 315; adjusting the exposure gain level, as indicated by block 316; determining whether the temporal noise exceeds a given threshold, as indicated by block 317; if the temporal noise fails to exceed the given threshold, detecting temporal noise in an image, as indicated by block 301, or, if the temporal noise exceeds the given threshold, determining whether brightness and contrast are optimized, as indicated by block 318; adjusting the gain level, as indicated by block 319; and re-detecting temporal noise, as indicated by block 301, in accordance with an embodiment of the present disclosure.

Still referring to FIG. 8, and referring back to FIG. 6, in an example of executing the method M2, the system S adaptively modifies power to lower temporal noise, wherein a hierarchical structure is used. In executing the method M2, illumination should be set as high as is comfortable to a user, considering a distance for which illumination is increasable without harming the patient. In executing the method M2, the cognitive optical system S considers various parameters in the optical chain, such as a zoom level and a numerical aperture in relation to the optical system 30, an exposure time, an exposure gain and de-noising strength, and a local area contrast enhancement strength in relation to the camera system 20, as well as brightness and contrast in relation to the display device 50. For each parameter, optimal settings may be based on "a priori" information learned from image drive informatics.

Referring back to FIGS. 1-8, in yet other embodiments of the present disclosure, user experience may be obtained and applied by the system S in executing the method M2 to automate adjustment of variables to optimize the signal-to-noise ratio (SNR) in entire volume in relation to either user-selected, or a user-defined region of interest (ROI) within given volume segments. The system S considers, not only the optical chain, but payload information, robotic arm information, and monitor information as well. The processor 10 receives input from the preoperative input device 60 and the intraoperative input device 70, wherein the intraoperative input device 70 receives input from at least one component, such as the navigation devices or external devices 80 and advanced optical or spectroscopic devices 90.

Still referring back to FIGS. 1-8, the processor 10 is further configured to determine whether an image is representative of the actual volume of view (VoV), e.g., by using image variables, such as tissue type, e.g., brain tissue, liver tissue, etc., and pathological type, by using factors that are intrinsic to an image, in comparison with factors that are related to the optical chain and with environmental factors, wherein an image can be automatically adjusted with an option of being manually overridden if necessary. The set of executable instructions comprises a macro template set for setting macro conditions. Instructions for interrogation of pathology sets global conditions, e.g., wherein the optical chain, the ambiance, and the room environment, that inform a setting for the intensity and for optimizing gain in relation to biological materials present, e.g., lipids, etc.

Still referring back to FIGS. 1-8, the processor 10 is further configured to provide instructions to other system devices for increasing navigation accuracy, thereby improving acquisition of incremental data, as the imaging proceeds into the VoV, whereby the optical chain interrogates the tissue in the VoV in real-time (dynamic interrogation). By so doing, the system S provides dynamic adjustment that is informatics-based in real-time and that is ROI-dependent. The system S also involves a user-defined ROI running in the background, whereby a dynamic automated adjustment of the optical chain and real-time video processing is performed. The processor 10 is further configured to provide an instruction for adjusting optical parameters based on ambiance, biology, pathology, e.g., by determining whether the image has a correct color contrast and whether the image has a correct SNR based on a given pathology. The processor 10 is further configured to provide an instruction for effecting micro-adjustments, for changing dimensions, e.g., whether to proceed in the near-infrared (NIR) or whether to proceed with hyperspectral imaging, whereby an adjusted image is displayable that better represents an image that is captured by a naked eye. The processor 10 is further configured to provide instructions for tuning, or fine-tuning, color separation, gamut, for optimizing and enhancing contrast, whereby an adjusted image is enhanced beyond an image that is captured by a naked eye.

Still referring back to FIGS. 1-8, the processor 10 is further configured to provide instructions for automatically adjusting magnification after the ROI has been defined, e.g., automatically adjusting parameters, such as zoom and working distance, and for digitally adjusting the camera device 20. The processor 10 is further configured to provide instructions: for defining the ROI, adjusting a first parameter, then adjusting the first parameter based on the SNR, for building the hierarchical structure to optimize the SNR, for effecting micro-adjustments of components, such as optical coherence tomography (OCT), an imaging system, and advanced optics, for providing tissue composition information, for providing feedback as a "truth" source, and for optimizing conspicuity (conspicuousness) of the ROI by performing iterative interrogations.

Still referring back to FIGS. 1-8, the processor 10 is further configured to provide instructions: for determining whether an MRI displays fat in a tumor at macroscopic level, e.g., by initially using macro optics (at the beginning of cases adjusted) based on pathology, for acquiring a specimen, for transmitting the specimen to an imaging system, whereby the imaging system provides imaging that indicates a high lipid and calcium content, by example only, for transmitting the information relating the high lipid and calcium content to an automated positioning system, whereby the automated positioning system creates a new micro-environment by adjusting the optical chain via further image processing, whereby the representation of the lipid becomes more conspicuous, i.e., easier to see, wherein adjusting the optical chain via further image processing comprises working, adjusting, and using multi-modal information, and wherein adjustments are hierarchical.

Still referring back to FIGS. 1-8, in a red environment, e.g., a blood environment, the processor 10 is further configured to provide instructions for prompting irrigating the red environment with water, wherein determining whether irrigation is necessary comprises using a photometer). In a surgical procedure, a major challenge in image processing relates to tissue heterogeneity (not all parts of a given tissue appear the same). To address at least this challenge, the processor 10 is further configured to provide instructions for displaying a dashboard of suggested actions, e.g., Siri for operation, for obtaining inputs from multi-modal sources, for providing output to effect optical chain video adjustment, for initially tuning all parameters, whereby further image processing is effected only as a last resort, thereby minimizing the degree of "untruth" in an image. Specifically, in a blood environment, the processor 10 is further configured to provide instructions for monitoring inputs from all other components, whereby the system S acts as an imaging "watchdog."

At least some aspects disclosed are embodied, at least in part, in software. That is, some disclosed techniques and methods are carried out in a computer system or other data processing system in response to its processor, such as a microprocessor, executing sequences of instructions contained in a memory, such as ROM, volatile RAM, non-volatile memory, cache or a remote storage device.

A computer readable storage medium is used to store software and data which when executed by a data processing system causes the system to perform various methods or techniques of the present disclosure. The executable software and data is stored in various places including for example ROM, volatile RAM, non-volatile memory and/or cache. Portions of this software and/or data are stored in any one of these storage devices.

Examples of computer-readable storage media may include, but are not limited to, recordable and non-recordable type media such as volatile and non-volatile memory devices, ROM, RAM, flash memory devices, floppy and other removable disks, magnetic disk storage media, optical storage media, e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium is the internet cloud, or a computer readable storage medium such as a disc.

Furthermore, at least some of the methods described herein are capable of being distributed in a computer program product comprising a computer readable medium that bears computer usable instructions for execution by one or more processors, to perform aspects of the methods described. The medium is provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer usable instructions may also be in various forms, including compiled and non-compiled code.

At least some of the elements of the systems described herein are implemented by software, or a combination of software and hardware. Elements of the system that are implemented via software are written in a high-level procedural language such as object oriented programming or a scripting language. Accordingly, the program code is written in C, C++, J++, or any other suitable programming language and may comprise modules or classes, as is known to those skilled in object oriented programming. At least some of the elements of the system that are implemented via software are written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information, as herein shown and described in detail, is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the present disclosure.

INDUSTRIAL APPLICABILITY

Generally, the present disclosure industrially applies to medical imaging systems. More particularly, the present disclosure industrially applies to control of optical systems for medical imaging systems. Even more particularly, the present disclosure industrially applies to smart control of optical systems for medical imaging systems.

What is claimed:

1. A cognitive optical system for dynamically refining an image, having at least one imaging parameter, during a medical procedure, the system comprising:
   a processor operable by a set of executable instructions storable in relation to a non-transitory memory device and configured to automatically adjust the image by fine-tuning an optical chain based on at least one input parameter,
   the processor configured to fine-tune the optical chain by using at least one of a machine learning technique and an artificial intelligence technique,
   the processor configured to perform any dynamic parameter adjustment by using a hierarchal structure, whereby optimization degradation of one imaging parameter of the at least one imaging parameter by optimization of another imaging parameter of the at least one imaging parameter is avoided, and
   the processor configured to fine-tune the optical chain by effecting micro-adjustments thereto.

2. The system of claim 1,
   wherein the processor is further configured to automatically adjust the image by:
   automatically compensating for at least one external factor affecting an anatomical area being viewed;
   automatically adjusting the at least one imaging parameter;
   automatically adjusting at least one internal control of the optical chain,
   automatically adjust the image based on the at least one input parameter, the at least one input parameter comprising at least one of a host tissue type, a pathology type, an optical chain variable, and a plurality of user experience data via a preoperative input device, and
   at least one of receive input from, and transmit output to, an intraoperative input device, the intraoperative input device receiving the input from a plurality of components, the plurality of components comprising at least one navigation device and at least one external device, and the plurality of components further comprising one of at least one advanced optical device and at least one spectroscopic device, and
   wherein the optical chain comprises at least one of optical software, optical firmware, and optical hardware.

3. The system of claim 1,
   wherein the at least one imaging parameter comprises at least one of an illumination, a saturation, a color, a contrast, and an opacity, and
   wherein the processor is further configured to at least one of: automatically adjust the illumination by adjusting at least one of an illumination spectrum and a luminance in relation to a camera scope, automatically adjust the color by adjusting at least one color filter in relation to a camera scope, automatically adjust the saturation by processing the image to reduce light, and automatically adjust the opacity by at least one of adjusting an infrared illumination level and applying a filter.

4. The system of claim 1, wherein the processor is further configured to automatically adjust the image based on the at least one input parameter further comprising an environmental condition.

5. The system of claim 1, wherein the set of executable instructions comprises a predictive macro-optimization instruction based on a multi-modal real-time tissue interrogation for facilitating dynamically refining imaging.

6. The system of claim 5, wherein the predictive macro-optimization instruction comprises informatics, whereby the processor is configured to determine at least one ideal condition corresponding to the at least one external factor.

7. The system of claim 1, wherein the processor is configured to instruct an imaging system to provide a prompt requesting approval of an automated adjustment of the at least one imaging parameter prior to rendering an adjusted image on a display device.

8. The system of claim 6, wherein the informatics comprises a feature for learning information relating to previous procedures.

9. The system of claim 8, wherein the information relating to the previous procedures comprises at least one type of imaging parameter for optimizing tissue differentiation.

10. The system of claim 1, wherein the at least one internal control of the optical chain comprises at least one of a zoom level, a numerical aperture, a camera type, an exposure time, an exposure gain, a de-noising strength, a local area contrast enhancement strength, a display type, a brightness level, and a contrast level.

11. A method of fabricating a cognitive optical system for dynamically refining an image, corresponding to at least one imaging parameter, during a medical procedure, the method comprising:
   providing a processor operable by a set of executable instructions storable in relation to a non-transitory memory device and configured to automatically adjust the image by fine-tuning an optical chain based on at least one input parameter,
   providing the processor comprising configuring the processor to fine-tune the optical chain by using at least one of a machine learning technique and an artificial intelligence technique,
   providing the processor comprising configuring the processor to perform any dynamic parameter adjustment by using a hierarchal structure, whereby optimization degradation of one imaging parameter of the at least one imaging parameter by optimization of another imaging parameter of the at least one imaging parameter is avoided, and
   providing the processor comprising configuring the processor to fine-tune the optical chain by effecting micro-adjustments thereto.

12. The method of claim 11,
wherein providing the processor further comprises configuring the processor to automatically adjust the image by:
automatically compensating for at least one external factor affecting an anatomical area being viewed;
automatically adjusting the at least one imaging parameter;
automatically adjusting at least one internal control of the optical chain,
automatically adjust the image based on the at least one input parameter, the at least one input parameter comprising at least one of a host tissue type, a pathology type, an optical chain variable, and a plurality of user experience data via a preoperative input device, and
at least one of receive input from, and transmit output to, an intraoperative input device, the intraoperative input device receiving the input from a plurality of components, the plurality of components comprising at least one navigation device and at least one external device, and the plurality of components further comprising one of at least one advanced optical device and at least one spectroscopic device; and
adjust the image by fine-tuning the optical chain, comprising at least one of optical software, optical firmware, and optical hardware, based on at least one input parameter.

13. The method of claim 11,
wherein providing the processor comprises configuring the processor to automatically adjust the at least one imaging parameter comprising at least one of an illumination, a saturation, a color, a contrast, and an opacity, and
wherein providing the processor comprises configuring the processor to at least one of: automatically adjust the illumination by adjusting at least one of an illumination spectrum and a luminance in relation to a camera scope; automatically adjust the color by adjusting at least one color filter in relation to a camera scope; automatically adjust the saturation by processing the image to reduce light; and automatically adjust the opacity by at least one of adjusting an infrared illumination level and applying a filter.

14. The method of claim 11, wherein providing the processor further comprises configuring the processor to automatically adjust the image based on the at least one input parameter further comprising an environmental condition.

15. The method of claim 11, wherein providing the processor comprises configuring the processor as operable by the set of executable instructions comprising a predictive macro-optimization instruction based on a multi-modal real-time tissue interrogation for facilitating dynamically refining imaging.

16. The method of claim 15, wherein providing the processor comprises configuring the processor as operable by the set of executable instructions comprising the predictive macro-optimization instruction, the predictive macro-optimization instruction comprising an instruction for using informatics, whereby the processor is configured to determine at least one ideal condition corresponding to the at least one external factor.

17. The method of claim 11, wherein providing the processor comprises configuring the processor to instruct an imaging system to provide a prompt requesting approval of an automated adjustment of the at least one imaging parameter prior to rendering an adjusted image on a display device.

18. The method of claim 16,
wherein configuring the processor as operable by the set of executable instructions comprises providing a predictive macro-optimization instruction, the predictive macro-optimization instruction comprising an instruction for using informatics, the instruction for using informatics comprising providing a feature for learning information relating to previous procedures, and
wherein the information relating to previous procedures comprises at least one type of imaging parameter for optimizing tissue differentiation.

19. The method of claim 11, wherein the at least one internal control of the optical chain comprises at least one of a zoom level, a numerical aperture, a camera type, an exposure time, an exposure gain, a de-noising strength, a local area contrast enhancement strength, a display type, a brightness level, and a contrast level.

20. A method of dynamically refining an image, corresponding to at least one imaging parameter, during a medical procedure by way of a cognitive optical system, comprising:
providing the cognitive optical system, providing the cognitive optical system comprising providing a processor operable by a set of executable instructions storable in relation to a non-transitory memory device and configured to automatically adjust the image by fine-tuning an optical chain based on at least one input parameter,
providing the processor comprising configuring the processor to fine-tune the optical chain by using at least one of a machine learning technique and an artificial intelligence technique,
providing the processor comprising configuring the processor to perform any dynamic parameter adjustment by using a hierarchal structure, whereby optimization degradation of one imaging parameter of the at least one imaging parameter by optimization of another imaging parameter of the at least one imaging parameter is avoided, and
providing the processor comprising configuring the processor to fine-tune the optical chain by effecting microadjustments thereto; and
operating the processor.

* * * * *